United States Patent [19]
Ophir

[11] Patent Number: 4,807,635
[45] Date of Patent: * Feb. 28, 1989

[54] PULSE CENTROID ECHO METHOD AND APPARATUS FOR ENHANCED SOUND VELOCITY ESTIMATION IN VIVO

[75] Inventor: Jonathan Ophir, Houston, Tex.

[73] Assignee: Board of Regents, The University of Texas System, Austin, Tex.

[ * ] Notice: The portion of the term of this patent subsequent to Jun. 2, 2004 has been disclaimed.

[21] Appl. No.: 887,349

[22] Filed: Jul. 21, 1986

Related U.S. Application Data

[63] Continuation-in-part of Ser. No. 823,332, Jan. 28, 1986, which is a continuation-in-part of Ser. No. 791,719, Oct. 28, 1985, Pat. No. 4,669,482.

[51] Int. Cl.$^4$ .............................................. A61B 10/00
[52] U.S. Cl. .................................. 128/660.01; 73/597; 73/602
[58] Field of Search .................. 128/660, 661; 73/597, 73/599, 602

[56] References Cited

U.S. PATENT DOCUMENTS

| | | |
|---|---|---|
| 3,388,372 | 6/1968 | De Witz . |
| 4,395,909 | 8/1983 | Steinberg et al. . |
| 4,625,555 | 12/1986 | Fujii ..................................... 73/597 |
| 4,669,482 | 6/1987 | Ophir ................................. 128/660 |

FOREIGN PATENT DOCUMENTS

| | | |
|---|---|---|
| 0152874 | 8/1985 | European Pat. Off. . |
| 3518526 | 1/1986 | Fed. Rep. of Germany . |
| 3446594 | 7/1986 | Fed. Rep. of Germany . |
| 8401432 | 8/1984 | PCT Int'l Appl. . |

*Primary Examiner*—Francis J. Jaworski
*Attorney, Agent, or Firm*—Arnold, White & Durkee

[57] ABSTRACT

A method and apparatus of enhancing the accuracy of in vivo sound velocity estimation by identifying segments of different sound velocity along a tracked ultrasound beam. The effects of refraction on the tracked beam at the interface between tissue regions are estimated. Also disclosed is a technique for estimating the refractive effects of naturally occurring and artificially introduced acoustical contrast fluids. The accuracy of the sound velocity measurements is increased by utilizing the centroid-to-centroid distance between the pulses produced by ultrasound sending and receiving transducers in calculating the ultrasound beam velocity.

15 Claims, 5 Drawing Sheets

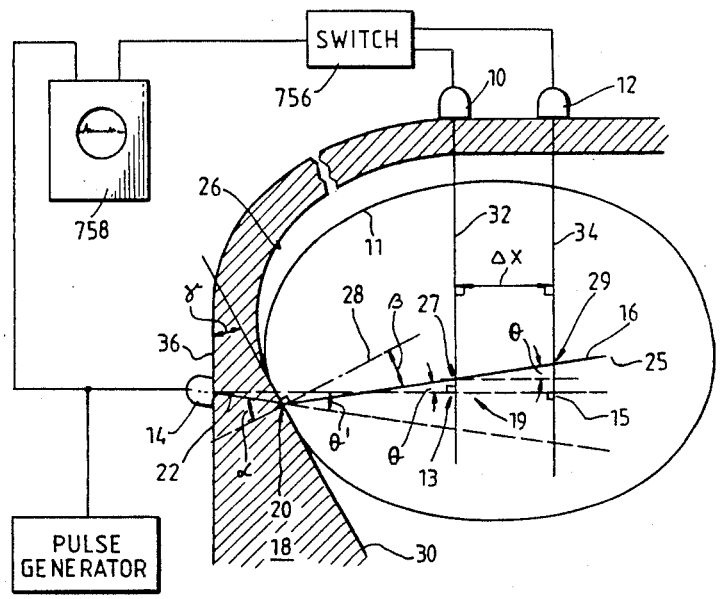
*Fig. 1B*
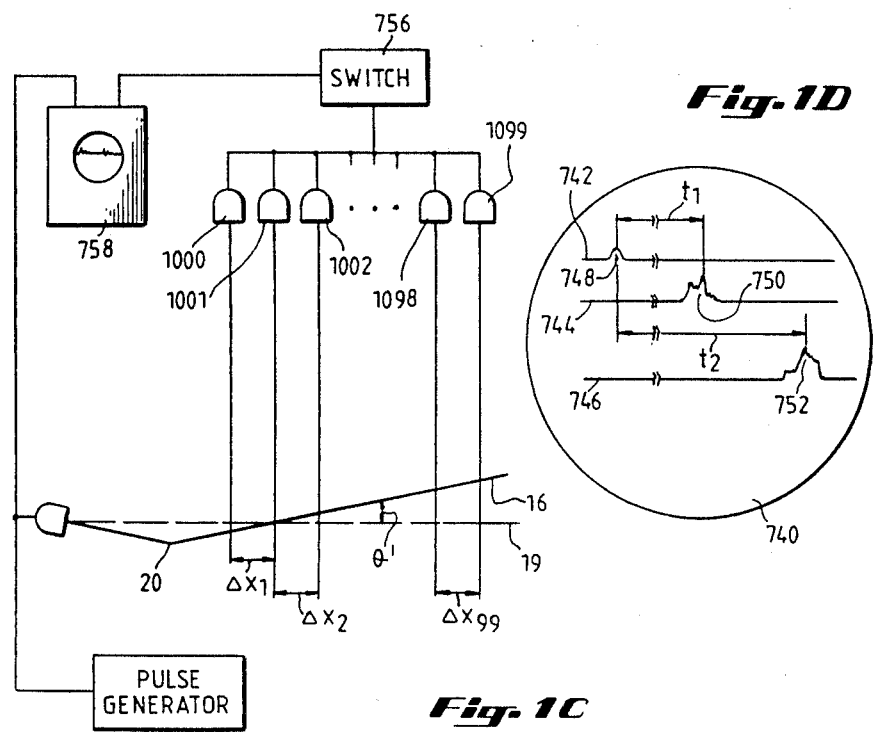
*Fig. 1D*
*Fig. 1C*

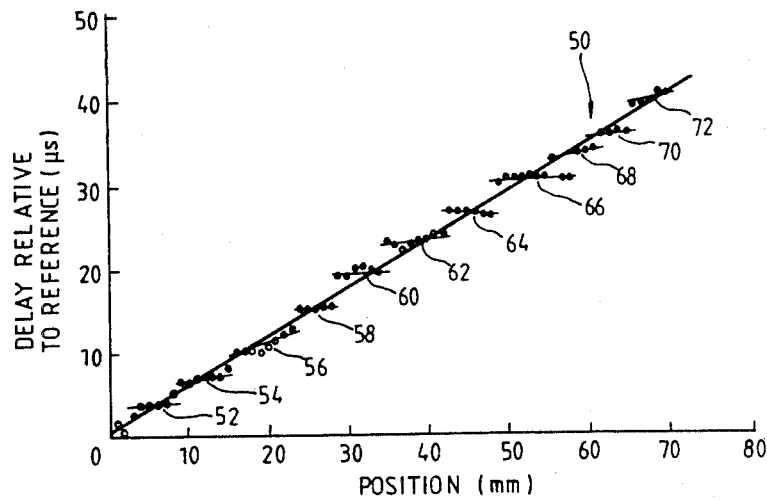
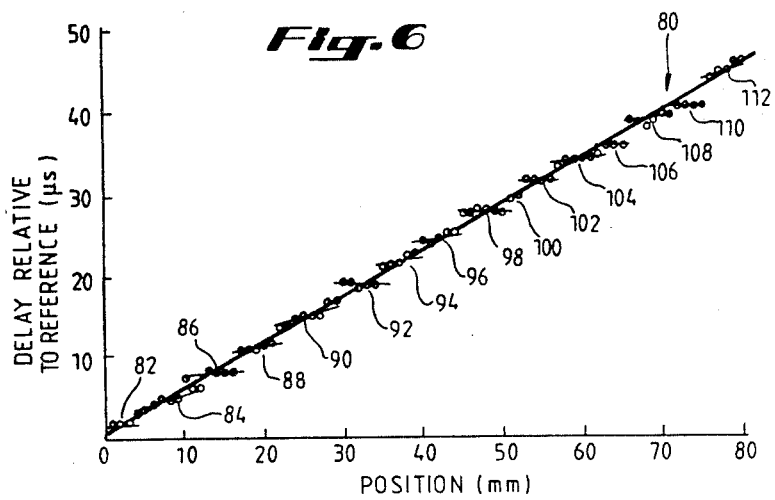

PULSE CENTROID ECHO METHOD AND APPARATUS FOR ENHANCED SOUND VELOCITY ESTIMATION IN VIVO

CROSS-REFERENCE TO RELATED APPLICATIONS

This application is a continuation-in-part of U.S. application Ser. No. 823,332 entitled Method for Enhancing the Accuracy of In Vivo Sound Velocity Estimation filed Jan. 28, 1986 which in turn is a continuation-in-part of U.S. Ser. No. 791,719 filed Oct. 28, 1985, now U.S. Pat. No. 4,669,482. Applicant incorporates said application Ser. Nos. 791,719 and 823,332 by reference herein and claims the benefit of said applications for all purposes pursuant to 37 C.F.R. §1.78.

BACKGROUND OF THE INVENTION

1. Field of the Invention

This invention relates to a method and apparatus for enhancing the accuracy of sound velocity measurements made in organic tissue using ultrasound means. More particularly, this invention relates to a method and apparatus for estimating the change in velocity of ultrasound energy as it passes through and is refracted by multiple tissue layers.

2. Description of the Prior Art

Ultrasound techniques have been extensively used in the field of diagnostic medicine as a nontoxic means of analyzing the properties of in vivo (i.e., living) tissue. Ultrasound can be used for both tissue imaging as well as the measurement of the speed of sound in organic tissue. In particular, the speed of sound in an organ can be one indication of the presence of disease within that organ.

A human or animal body represents a nonhomogeneous medium for the propagation of ultrasound energy. The internal area of the body is comprised of a plurality of regions representing different organs, tissue layers, and bone. The speed of sound within each of these layers is, in general, different from that of adjacent regions. As an ultrasound beam passes through the various regions internal to the body, these differing speeds of sound result in the refraction of the ultrasound beam. The beam will, in general, undergo bending at the interface between two such regions. Problems with compensating for refraction have limited the accuracy and effectiveness of ultrasound techniques in the medical diagnostic field.

One principal source of refraction is the layer of fat contained in the tissue wall surrounding the body. This layer can be up to several centimeters thick and will generally have a speed of sound different from that of the internal organs beneath the body fat layer. Also, the inner boundary of the body fat layer may be somewhat irregular. As the ultrasound beam is directed from a source transducer on the surface of the body skin through the fat layer and into internal organs, there is a refraction or bending of the beam as it passes through the inner boundary of the body fat layer.

For some ultrasound techniques utilizing intersecting ultrasound beams, refraction can be a source of inaccuracy. Inability to determine precisely how the various ultrasound beams will be bent may make actual intersection of the ultrasound beams difficult. In appropriate circumstances, the effects of refraction may simply be ignored. In other instances, a reasonable assumption can be made that parallel ultrasound beams are subject to equal bending due to refractive effects.

In many cases, however, a higher degree of accuracy may be obtained by estimating the extent to which ultrasound beams are bent due to significant refractors such as the inner boundary of the body wall. Additionally, there are circumstances under which introduction of refraction with acoustical contrast fluids can be used to enhance the accuracy of in vivo ultrasound examination.

The various effects of refraction on the accuracy of ultrasound examination of organic tissue are complex and frequently strongly interact with one another. Consequently, a single approach to the analysis of and correction for refraction is insufficient in the general case. The medical ultrasound researcher requires a battery of techniques, the techniques useable individually or in combination, to adequately deal with the almost infinite variety of refraction problems encountered in medical ultrasound analysis and diagnosis.

The medical ultrasound researcher relies upon sophisticated analytical techniques and formulas to reduce and interpret the data generated by ultrasound equipment. Conventional ultrasound data acquisition apparatus employs oscilloscopes electrically coupled to transducers. The physical composition of the human body, as well as that of lower life forms, produces nonuniform sound wave scattering which results in perturbations in the pulses displayed on the oscilloscope.

Many of the conventional ultrasound data acquisition methods measure pulse travel time, based upon the baseline-to-peak distance of pulses displayed on the oscilloscope. Baseline-to-peak based calculations of pulse travel time contain a degree of inaccuracy resulting from the nonuniform, jagged peaks of pulses produced by sound waves which have been scattered within the body.

SUMMARY OF THE INVENTION

The present invention discloses a pulse centroid echo method and apparatus for enhanced sound velocity estimation in vivo. This invention is suitable for use with the ultrasound analysis technique disclosed in my copending applications U.S. Ser. Nos. 791,719 and 823,332. The techniques disclosed herein are meant to be used individually or in various combinations to provide maximum flexibility in ultrasound analysis in vivo. According to the present invention, a method is presented wherein at least one tracked beam of ultrasound is directed into a region of interest within organic tissue, the beam being partitioned into contiguous segments. Each of the contiguous segments is defined by a region of tissue in which the velocity of sound is substantially different from adjacent neighbor tissue regions.

In one embodiment of the present invention, a tracked ultrasound beam is intersected by at least two tracking ultrasound beams within a region of interest in the organic tissue. The tracked beam is partitioned into at least two contiguous segments, the boundary between the two segments being the inner boundary of the body wall fat. A plurality of ultrasound pulse travel time measurements are made, each of the measurements made with a different apparent angle of intersection between the tracked beam and the tracking beam. For each of the plurality of measurements, techniques are employed for correcting refraction occurring in a transverse plane. Data pairs collected in the plurality of measurements are fitted to an appropriate equation using curve-fitting techniques ell known in the art, whereby the index of refraction at the body wall inner boundary, the inclination of the inner boundary, and the speed of sound in the internal tissue are derived.

In another embodiment of the invention, an analysis of plots of pulse travel time vs. pulse travel distance is used to derive an estimate of the volume density of inhomogeneities in tissue. These inhomogeneities, known in the art as "scatterers", produce stair steps in the distance vs. time plots. Analysis of the number and position of stair steps in conjunction with training sets of data permit estimates of the number and density of scatterers. Data training sets are compiled by determining the number of stair steps present in plots of a large collection of tissue samples.

In yet another embodiment of the invention, the tracked ultrasound beam is directed into a region of tissue containing an acoustical contrast fluid. Acoustical contrast fluids in this context may be either naturally occurring in the body or purposely injected therein in the course of ultrasound diagnosis and analysis. One example of a naturally occurring acoustical contrast fluid is the nitrogen formed in the bloodstream when the body is subjected to decompression. Artificially-introduced acoustical contrast fluids comprise liquids such as nontoxic glycerine solutions and perfluorocarbons. One or more of these liquids can be selected by the user to induce distortions in ultrasound images of the body's internal organs. Estimates of the speed of sound within those organs will permit determination of the volumetric concentration of the acoustical contrast fluid within the organ.

According to one aspect of the present invention, ultrasound imaging is used to locate a region of interest within tissue internal to the body before sound velocity estimates are made. According to another aspect of the present invention, the volume concentration of an acoustical contrast fluid introduced into organic tissue is measured by measuring the resulting change in ultrasound velocity.

It is thus a general object of this invention to provide the ultrasound researcher with an integrated set of techniques useable to enhance the accuracy of medical ultrasound analysis.

This invention employs a sending transducer and a series of receiving transducers, all of which are connected to an oscilloscope in a such a manner that pulses will be produced on the oscilloscope screen when each transducer sends or receives ultrasound energy. The time required for an ultrasound beam to travel from a sending transducer to a receiving transducer is calculated by measuring the distance on the ultrasound trace between the baseline and the pulse centroid. The change in ultrasound beam velocity is determined by comparing the time required for an ultrasound beam to travel from the sending transducer o various receiving transducers.

Other objects and advantages and a more complete understanding of the invention may be obtained by referring to the following detailed description of a preferred embodiment when taken in conjunction with the accompanying drawings.

BRIEF DESCRIPTION OF THE DRAWINGS

FIG. 1B shows an embodiment of FIG. 1 with the addition of a pulse generator, oscilloscope and switching apparatus to measure the refractive effects of the fat layer within the body wall.

FIG. 1C shows the embodiment of FIG. 1B modified to have a large number of tracking beams.

FIG. 1D shows typical oscilloscope traces of incident and scattered energy pulses observed during the measurement process.

FIG. 5 shows stair steps occurring in a plot of distance vs. time data acquired with the configuration of FIG. 1 in 20 pores per linear inch foam containing a 50% glycerol solution.

FIG. 6 is a plot of data similar to that of FIG. 5 taken on 30 pores per linear inch foam containing a 50% glycerol solution.

DESCRIPTION OF THE PREFERRED EMBODIMENTS

According to the present invention, a tracked beam of ultrasound energy is directed into a tissue region within the body. The tracked beam of ultrasound energy will pass through a plurality of tissue regions, each region having a different estimated velocity of sound. The present invention is directed to partitioning the tracked beam into contiguous segments. That is, the segments of the tracked beam lying in each of the tissue regions of differing estimated velocity are located and identified.

REFRACTION DUE TO BODY WALL FAT

Figure 1:
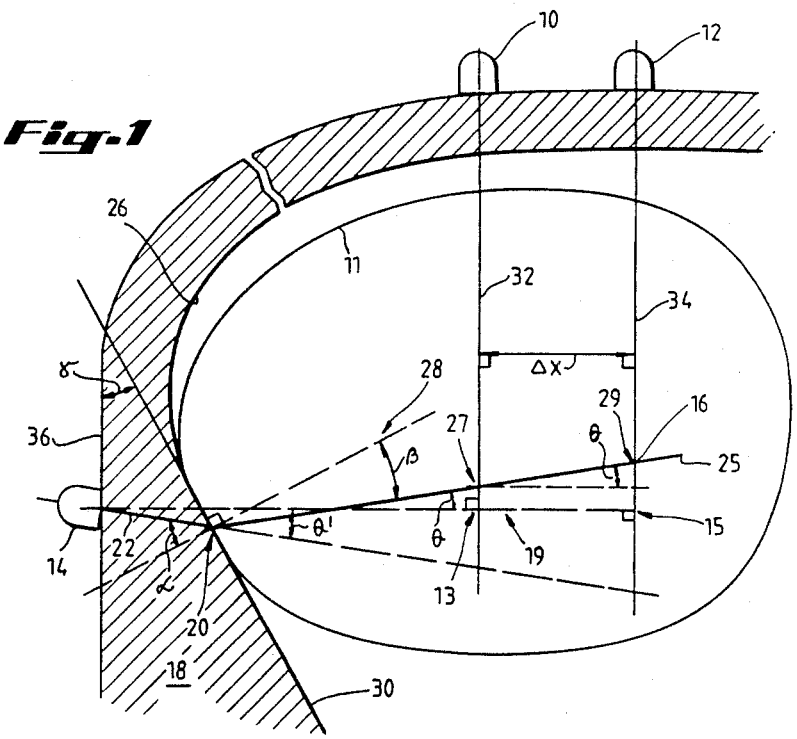
FIG. 1 shows an embodiment of the invention wherein refractive effects of the fat layer within the body wall are estimated.

With reference to FIG. 1, a tracked beam 16 produced by an ultrasound transducer 14 is directed into the body and intersects a tracking beam 32 at a point 27 and a tracking beam 34 at a point 29. The tracking beam 32 is produced by an ultrasound transducer 10 and the tracking beam 34 is produced by ultrasound transducer 12.

The ultrasound transducers 10, 12, and 14 are of a piezoelectric type well known in the ultrasound art. The transducers contain a crystal of a material such as quartz or other suitable material exhibiting a piezoelectric effect. That is, when an electric signal voltage is applied across the crystal, the crystal will mechanically vibrate responsive to the signal voltage. Conversely, when a mechanical vibration is applied to the crystal, a signal voltage will be present across the crystal responsive to the mechanical vibration. Transducers may therefore be used either to transmit or receive ultrasound energy.

In the embodiment of FIG. 1, the transducer 14 accepts an electrical pulse signal from a pulse generator 56 and produces an ultrasound pulse responsive thereto which is transmitted out along the tracked beam 16. The transducers 10 and 12 are configured to receive ultrasound energy scattered from the points 27 and 29 along tracking beams 32 and 34, respectively. It should be noted, however, that the embodiment of FIG. 1 would work equally well if transducers 10 and 12 were configured to transmit ultrasound energy and transducer 14 was configured to receive ultrasound energy. Thus, a tracked beam may be a transmitted beam or may be a received beam. Similarly, tracking beams may be transmitted beams as well as received beams.

The transducers 10, 12, and 14 are applied to the outer skin 36 of a human body. The body is surrounded by a body wall 18 which is defined by an inner boundary 26. As seen in FIG. 1, the tracked beam 16 comprises two contiguous segments. The segment 22 extends from the transducer 14 to the point 20 on the inner boundary 26. The segment 24, the nearest neighbor segment to the segment 22, extends from the point 20 to the point 25. The segment 24 is assumed to lie within the liver 11. The liver 11 is seen to lie very close to the inner boundary 26 of the body wall 18.

The speed of sound in the body wall 18 is different from that in the liver 11. Consequently, the tracked beam 16 undergoes refraction or bending at the point 20.

The tracked beam is directed into the body wall 18 at angle of incidence $\theta'$ measured from a line 19. The line 19 intersects the tracking beam 32 at a right angle at the point 13 and intersects the tracking beam 34 at a right angle at the point 15.

Because of the refraction, the tracked beam 16 actually intersects the tracking beams 32 and 34 at an angle of $(90° - \theta)$ as shown in FIG. 1. The tracking beams 32 and 34 are assumed to be parallel and separated by a distance $\Delta X$. The segment 22 makes an angle of $\theta'$ with the axis 19. A line 30 is drawn tangent to the inner wall 26 at the point 20. A second line 28 passes through the point 20 normal to the line 30. The lines 28 and 30 provide axes for the measurement of the refraction angles $\alpha$ and $\beta$.

An index of refraction n is associated with the interface between the body wall 18 and the liver 11. From Snell's law:

$$\frac{\sin \alpha}{\sin \beta} = n.$$

Assuming that $\alpha$ and $\beta$ are angles less than approximately 5°, $\sin \alpha = \alpha$ and $\sin \beta = \beta$. Thus, the index of refraction n is approximately equal to $\alpha/\beta$.

From the geometry of the configuration in FIG. 1, it is apparent that $$\alpha = \beta + \theta - \theta'$$

Noting that the above-recited relationship exists between the angles $\alpha$ and $\beta$, and the index of refraction n, $$\theta = \left(1 - \frac{1}{n}\right)\alpha + \theta'$$

Again referring to the geometry of FIG. 1, the angle representing the inclination of the inner boundary 26 at the point 20 is related to $\theta'$ and $\alpha$ by $$\alpha = \gamma - \theta'.$$

Through obvious algebraic manipulations of the above recited equations, $$\theta = K_0 + K_1 \theta'$$

where $$K_0 = 1 - {}_n{}^l)$$

and $$K_1 = ({}_n{}^l)$$

Using the configuration of FIG. 1, a first travel time $t_1$ may be measured. The travel time $t_1$ is the time required for a pulse of ultrasound energy to travel from transducer 14 along tracked beam 16 to point 27 and be scattered therefrom along tracking beam 32 to transducer 10. A second travel time, $t_2$, may then be measured. The travel time $t_2$ is defined as the time required for a pulse of ultrasound energy to travel from transducer 14 along tracked beam 16 to point 29, and be scattered therefrom along the tracking beam 34 to transducer 12. The difference between these two travel times is denoted by $\Delta t$. The average speed of sound along the tracked beam 16 between the points 27 and 29 will be denoted $\hat{c}$.

As previously stated, a tracked beam and a tracking beam may be a transmitted beam or a received beam. Thus, the sequence previously described in which pulses of ultrasound energy are emitted from transducer 14 and received by transducers 10 and 12, respectively, may be reversed. Such a reversal will produce a sister data point, $\Delta t$, from which the average speed of sound along the tracked beam 16 between the points 27 and 29, $\hat{c}$, can be ascertained.

The statistical accuracy of the methods disclosed herein can be increased by reversing the direction of ultrasound beam travel and taking sister $\Delta t$ measurements for each $\Delta x$ increment as described below. This reversal process can be used repeatedly to yield multiple sister $\Delta t$ measurements, thus further enhancing the statistical accuracy of the methods disclosed in this application.

From geometric considerations obviously inherent in the configuration of FIG. 1, $$\Delta t = \frac{\Delta X}{\hat{c}} \frac{1 + \sin \theta}{\cos \theta}$$

By means of substitution of previously derived equations, $$\Delta t = \frac{\Delta X}{\hat{c}} \frac{1 + \sin (K_0 + K_1 \theta')}{\cos (K_0 + K_1 \theta')} \quad (1)$$

Figure 2:
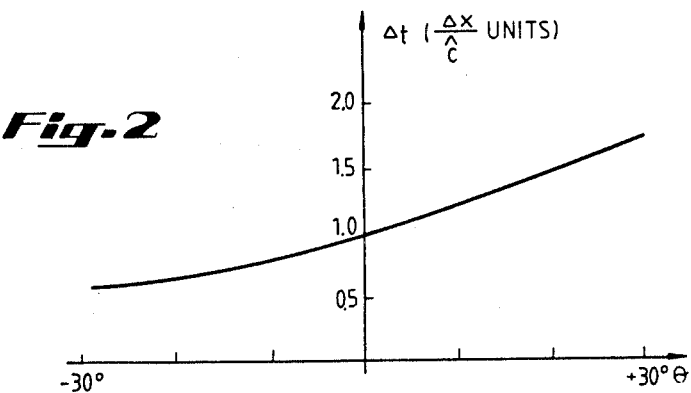
FIG. 2 shows a graph of an equation to which data pairs acquired using the configuration of FIG. 1 are fitted.

The graph of FIG. 2 is derived by plotting $\Delta t$ (in units of $\Delta X/\hat{c}$) and $\theta'$ (in degrees). A plurality of data pairs may be collected and fitted to the equation (1) whereby estimates of $\hat{c}$, $K_0$ and $K_1$ may be obtained. From $K_0$ and $K_1$, the index of refraction n and the angle $\gamma$ of the inclination of the inner boundary 26 at the point 20 may be obtained.

Where sister pairs of data points are taken, the plotting technique described above may be employed for each set of data points. This will produce a linear plot for each sister set of data points. Statistical analysis techniques, well known in the art, can then be employed to reduce the multiple data sets.

For simplicity, the measurement method is described as performed with a single pair of tracking beam transducers. The accuracy of the measurement of $\Delta t$ may be further improved by using a larger number of tracking beams transducers. If, for example, 100 tracking beam transducers are arranged in a linear array, the tracking beams of the transducers in the array intersecting the tracked beam at 100 points, a plurality of segments $\{\Delta X_i\}$ are defined. A plurality of travel time differences $\{\Delta t_i\}$ may be measured and an average $\Delta t$ may be obtained.

Figure 1A:
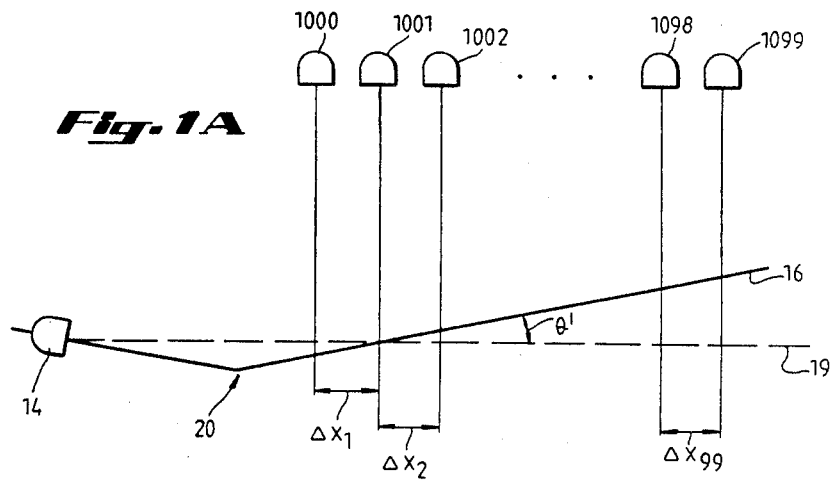
FIG. 1A shows, the embodiment of FIG. 1 modified to have a larger number of tracking beams.

Referring now to FIG. 1A, the two tracking beam transducers 10 and 12 have been replaced by 100 tracking beam transducers 1000 through 1099. The tracked beam 16 is shown refracted at the point 20 as in FIG. 1, but the body wall 18 and the liver 11 are not shown. A plurality of equal length segments $\Delta X_1$ through $\Delta X_{99}$ are defined by the intersection of the 100 tracking beams with the tracked beam 16. A travel time difference $\Delta t_i$, $i=1$ to 99, corresponding to each of the segments $\Delta X_i$ in a manner as disclosed for the case of two tracking beams. The average travel time, $$\Delta t = \frac{1}{99} \sum_{i=1}^{99} t_i,$$

is recorded along with the angle $\theta'$ to form a data pair.

Each of the data pairs collected comprise an angle of incidence $\theta'$ together with a travel time difference $\Delta t$ (or $\Delta \hat{t}$) measured for that value of $\theta'$. The angle $\theta'$ is defined by the physical arrangement of the transducers 10, 12, and 14. The travel times $t_1$ and $t_2$ may be measured by any appropriate means such as with a cathode ray oscilloscope in a manner described in my copending U.S. patent application No. 791,719. That is, an electrical signal conducted into transducer 14 to produce the ultrasound pulse traveling along the tracked beam 16 may be viewed in time reference on an oscilloscope screen with electrical pulses from transducers 10 and 12 representing scattered energy received, whereby the travel time $\Delta t$ may be measured. Persons skilled in the art will be aware of other suitable measurement techniques.

Equation (1) is fitted to the data pairs collected by adjustments of the coefficients $\hat{c}$, $K_0$, and $K_1$. Nonlinear least squares numerical techniques well known in the art may be used to select these three coefficients to minimize the error E, defined by the equation $$E = \sum_{i=1}^{N} \left[ \Delta t_i - \frac{\Delta X}{\hat{c}} \frac{1 + \sin(K_0 + K_1 \theta'_i)}{\cos(K_0 + K_1 \theta'_i)} \right]^2 \quad (2)$$

where $\theta'_i$, $\Delta t_i$ represent the N data pairs.

Figure 3:
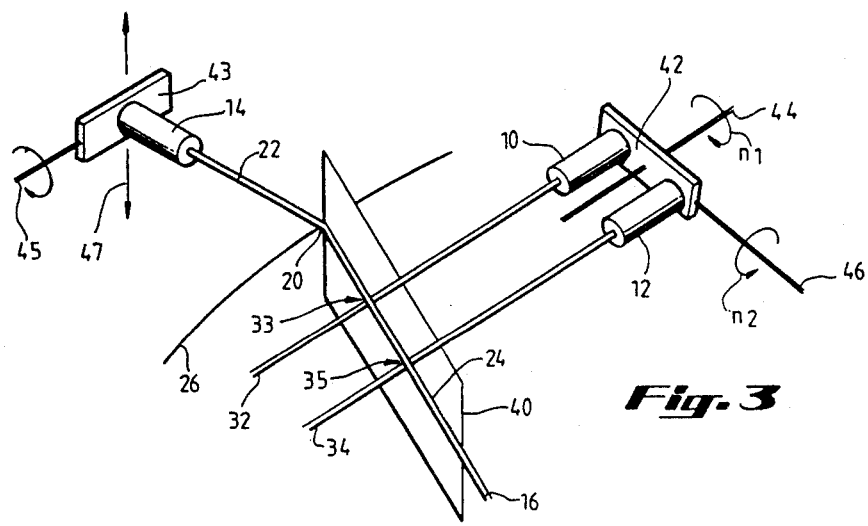
FIG. 3 shows a method of correcting for transverse plane refraction in the configuration of FIG. 1.

With reference to FIG. 3, a transverse plane 40 is defined by the segment 24 of the tracked beam 16, because of the bending of the tracked beam 16 at the point 20, the tracking beam 32 only partially intersects the tracked beam 16. The position of the transducers 10 and 12 may be adjusted whereby the degree of intersection will be corrected.

In FIG. 3, the transducers 10 and 12 are mounted rigidly to a base 42 rotatable about an axis 44 and an axis 46. Rotation of the base 42 about the axis 44 defines a roll angle $\eta_1$. Rotation of the base 42 about the axis 46 defines a bearing angle $\eta_2$. The roll angle $\eta_1$ and the bearing angle $\eta_2$ may be adjusted so that both of the tracking beams 32 and 34 intersect the tracked beam 16. Alternatively, a base 43 on which the tracked beam transducer 14 is mounted may be rotated about an axis 45 and shifted along a path 47 until the tracking beams 32 and 34 intersect the tracked beam 16.

Figures 4A, 4B:
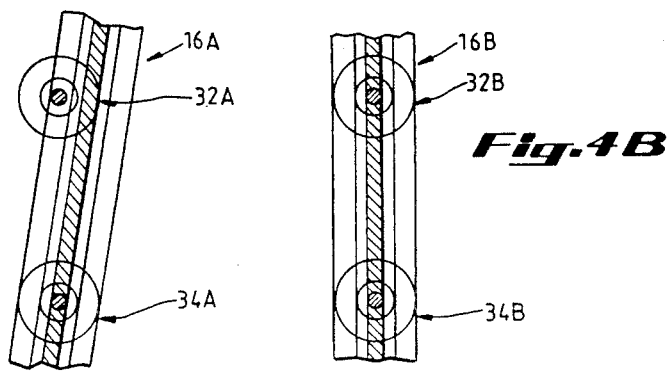
FIGS. 4A and 4B show the effects of transverse plane refraction on the intersection of the tracked and tracking beams shown in FIG. 1.

With reference to FIG. 4A, a tracked beam 16A is shown being perfectly intersected by a tracking beam 34A and partially intersected by a tracking beam 32A. The tracked beam 16A is longitudinal cross-section while the tracking beams 32A and 34A are shown in annular cross-section. FIG. 4B shows a tracked beam 16B being perfectly intersected by a pair of tracking beams 32B and 34B after orienting the transducers producing tracking beams 32B and 34B in the manner described below.

As each data pair $\{\theta'_i, \Delta t_i\}$ is collected, the ultrasound energy received at the transducers 10 and 12 must be observed. As previously indicated, one way of observing the time of arrival of ultrasound energy at the transducers 10 and 12 is to view the electrical pulse signals at these transducers responsive to the received ultrasound energy on cathode ray oscilloscope screen 54. The integrated pulse amplitudes of the electrical pulse signals, i.e., the area under the electrical pulses, is a measure of the degree of intersection of the tracking beam 16 and the tracked beams 32 and 34. Before a value for t is recorded, the angles $\eta_1$ and $\eta_2$ are adjusted so that the integrated pulse amplitudes are maximized. Alternatively, the position and orientation of the tracked beam transducer 14 is adjusted as previously described to maximize the integrated pulse amplitudes. A value of $\Delta t$ is then recorded together with the corresponding value of $\theta'$ for this data pair.

With reference to FIG. 1D, the travel times $t_1$ and $t_2$ may be measured by viewing the traces generated on an oscilloscope. Initially, the output of element 10 is selected by switch 756 to be conducted to and displayed by oscilloscope 758. An incident pulse, known as the baseline, emitted from transducer 14 is displayed at 748 on trace 742 on oscilloscope screen 740. The incident pulse travels along path 16 to reflection point 27 and some of the energy of the incident pulse is scattered along path 32 to transducer element 10. The energy received by element 10 is shown at 750 on trace 744 in FIG. 1D. Element 10 receives scattered energy from scatterers surrounding point 27, hence, the trace shows several jagged peaks at 750. The time $t_1$ is measured from the baseline, pulse 748, to the centroid of pulse 750. The pulse centroid occurs at a point $T_c$ such that:

$$T_c = \frac{\int f(t)\, t\, dt}{\int f(t)\, dt}$$

where f(t) is the magnitude of the pulse energy displayed on the oscilloscope trace as a function of time. The time $t_2$ is measured from the baseline, pulse 748, to the centroid of pulse 752.

The mathematical integration shown in the above equation for the calculation of $T_c$ can be performed with electronic circuits, such as integrators, widely known in the art. The integrations can also be performed with a variety of numerical analysis techniques. In the event that numerical methods are used to determine the pulse centroid locations, it would be desirable to have a hard copy of the oscilloscope trace. A hard copy could be obtained by installing a brush recorder, or equivalent device, in the oscilloscope, transducer circuit.

IDENTIFYING SCATTERERS FROM STAIR STEPS IN TIME VS. DISTANCE PLOTS

In the configuration of FIG. 1, a plurality of tracking beams may be used in conjunction with a tracked beam whereby the average velocity of sound along the tracked beam may be estimated. One such technique is disclosed in my copending U.S. patent application No. 791,719. As many as 100 or more tracking beams may be employed. A plurality of travel times measured from the transducer producing the tracked beam to each of a plurality of transducers producing the tracking beams may be recorded together with corresponding pulse travel distances along the tracked and tracking beams. The data pairs, each pair comprising a distance traveled and a corresponding time, are plotted on a time vs. distance graph.

With reference to FIG. 5, a time vs. distance plot is shown for sound velocity estimations made within an artificial tissue sample, or "phantom", comprising a 20-pore per linear inch (ppi) foam impregnated with a 50% glycerol solution at room temperature (approximately 21.5° C.). Approximately 70 tracking beams are employed and intersect the tracked beam at approximately 1 millimeter intervals. The horizontal axis of the graph indicates position in millimeters of beam intersections measured along the tracked beam from a reference point on the tracked beam. The vertical axis of the graph indicates the delay of an arrival time of a scattered pulse of ultrasound energy at a tracking beam transducer measured from a reference time. A plurality of circles representing actual measurements of time vs. position are plotted on the graph of FIG. 5. A straight line 50 is fitted to the plotted points utilizing a least squares error criterion.

It may be observed that plotted data points define a plurality of stair steps 52 through 72. That is, data points tend to cluster in identifiable groups, the slope of the a line fitted to data points in each group being different from the slope of the line fitted to all the data points. Approximately 11 stair steps appear over a distance along the tracked beam of approximately 70 millimeters. This is equivalent to approximately 3.9 stair steps per inch along the tracked beam. With reference to FIG. 6, a graph is obtained in a manner identical to that used to obtain the graph of FIG. 5. The graph of FIG. 6 represents data points acquired using 30 ppi foam impregnated with a 50% glycerol solution at room temperature. A line 80 is fitted to the points. Stair steps are still evident although they are more numerous than the stair steps appearing in FIG. 5. Also, the steps appear to comprise fewer data points each. In FIG. 6, approximately 16 stair steps 82 through 112 occur over a distance of 75 millimeters along the tracked beam. This is equivalent to approximately 5.4 stair steps per inch.

The foam pores filled with the glycerol solution comprise scatterers, which cause inhomogeneities in the foam-glycerol medium. It can be seen that in the 30 ppi foam, wherein the scatterers are smaller and more numerous, the resulting stair steps are likewise smaller and more numerous for a given distance along the tracked beam. By comparison, the smaller number of larger scatterers in the 20 ppi foam correspond to a smaller number of larger stair steps along the tracked beam. A scattering ratio, defined as the number of stair steps per inch along the tracked beam divided by the number of pores in the foam per linear inch, is approximately 0.19 for both types of foam filled with the 50% glycerol solution.

The estimated average velocity along the tracked beam in FIGS. 5 and 6 is the reciprocal of the slope of the straight line fitted to the data points. The respective slopes of the lines 50 and 80 are each seen to be substantially different from a line fitted to the data points of a single stair step. The estimated average velocity along the tracked beam within a segment defined by one stair step is seen to be substantially different from the estimated average sound velocity in an adjacent neighbor stair step. The tracked thus be thought of as being partitioned into segments of differing sound velocity due to the presence of scatters in the foam.

It is important to note that the scattering ratio for the 20 ppi foam is substantially equal to that for the 30 ppi foam, even through the pore densities and numbers of stair steps per unit length of tracked beam are not. The scattering ratio is thus seen to be a number related to the nature of the internal structure of the foam-glycerol material and has been normalized for the physical dimensions of the material's internal structure and for the particular type of ultrasound transducers used. My U.S. Pat. No. 4,406,153 discloses that ultrasound phantoms suitably impregnated with liquid may be used to very closely approximate the ultrasound transmission properties of organic tissue. Therefore, the scattering ratio measured for liquid impregnated foam may be used as a close approximation for the scattering ratio of organic tissue. Using this approximation, the actual number of scatterers per unit length in organic tissue may be obtained by dividing the number of stair steps found in time vs. distance plots taken for the tissue by the scattering ratio found for liquid impregnated foam.

Pathology in tissue frequently affects the tissue's consistency. For example, cirrotic liver tissue will generally be somewhat more tough and leathery than normal liver tissue. Other types of pathology may produce nodules or tumors within the tissue. This change in the tissue consistency will often manifest itself in a change in the velocity of ultrasound within the tissue. The change in tissue consistency may also affect the distribution of scatters within the tissue. However, the scattering ratio may reasonably be expected to remain substantially the same.

Thus, deriving a distance vs. time plot for an example of tissue and determining the number of stair steps per unit length in the plot may permit a direct estimation of the number of scatters per unit length within the tissue. The estimate of the number of scatters may be used to characterize the tissue for the presence of disease. The characterization requires that time vs. distance plots be compiled for training sets comprised of a large number of examples of tissue which are shown to be free of disease by diagnostic methods well known in the art. An average number of stair steps per unit length for the disease-free tissue may thus be computed from the distance vs. time plots. This average number of stair steps per unit length will be related to the average number of scatterers per unit length in the disease-free tissue by the scattering ratio (approximately 0.19) as previously disclosed. An average number of scatterers per unit length for diseased tissue may be similarly computed using a training set comprised of a large number of examples of diseased tissue.

An example of tissue under diagnosis may then be characterized as diseased or disease-free by comparing the average number of scatterers for the tissue under diagnosis with the averages computed for the training sets. Tissue examples for which the number of scatterers is closer to the average of diseased tissue will be categorized as diseased. Tissue having a number of scatterers closer to the average of relatively disease-free tissue will be categorized as disease free. It should be emphasized that this categorization as to the presence of disease in the tissue is meant to supplement rather than totally supplant other medical diagnostic techniques well known in the healing arts.

Alternatively, the above-described technique may be implemented using the number of stair steps per unit length found in distance vs. time plots without computation of the number of scatterers. An average number of stair steps may be computed for each of the training sets and the number of stair steps in a distance vs. time plot for an example of tissue under diagnosis may be compared directly to the training set stair step averages to accomplish the characterization.

The description of this embodiment of the invention has focused on use of plots of data points made on rectangular coordinates subjected to graphical analysis methods. It will be obvious to a person skilled in the art that other data manipulation methods, such as automatic computer analysis of the data points, may equally well be used. That is, "plotting" within this context also comprises arranging the data pairs in a data structure within a digital computer whereby the computer performs the analysis of stair steps as described herein without providing a visual display for a human operator to graphically analyze.

TRACKED BEAM PARTITIONING WITH ACOUSTICAL CONTRAST FLUIDS

Acoustical contrast fluids, both naturally occurring and artificially introduced, can change the velocity of sound within the tissue which is ultrasonically analyzed. When the velocity of sound within the acoustical contrast fluid is substantially different from that of the tissue into which the fluid is introduced, a variety of effects may be observed. One important example of a naturally occurring acoustical contrast fluid is the nitrogen formed in the bloodstream when the body is subjected to decompression. Additionally, a number of acoustical contrast liquids such as certain glycerine solutions and perfluorocarbons which are nontoxic to organic tissue may be artificially introduced into tissue and changes in the speed of sound may be observed.

A tracked ultrasound beam directed into a region of tissue containing a volume of acoustical contrast fluid will experience a change in velocity at the boundary of the region containing the fluid because of the substantial change in ultrasound velocity. The velocity change may be observed either through the estimation of ultrasound velocity as disclosed in my copending U.S. patent application No. 791,719, or through ultrasound imaging. In the typical ultrasound imaging case, a single set of ultrasound transducers are alternately switched between transmitting and receiving mode. Ultrasound energy is directed outward from the transducers along tracking beams to impinge upon the observed tissue region and be scattered back to the same ultrasound transducers along tracked beams. Depending upon the nature of the refraction present within the tissue, the tracked beams and tracking beams may or may not substantially coincide.

Figure 7:
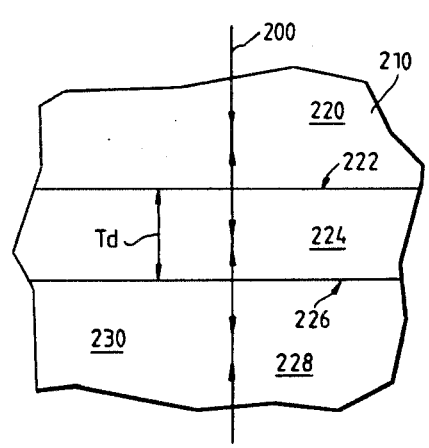
FIG. 7 shows a tissue region containing multiple tissue layers penetrated by an ultrasound beam in the absence of an acoustical contrast fluid.

In FIG. 7, ultrasound energy traverses a path 200 into a tissue region 210. The tissue region 210 is seen to be divided into a layer 220 adjacent to a layer 224 and separated therefrom by tissue interface 222. A tissue interface 226 separates the layer 224 from an adjacent layer 228. The path 200 is assumed to be normal to the interfaces 222 and 226. The interfaces 222 and 226 are further assumed to be parallel. Therefore, while the ultrasound energy travels at different speeds through the layers 220, 224, 228, the tracked and tracking beams will coincide along the path 200 without bending.

In general, ultrasound imaging will employ a plurality of tracked and tracking beams not shown in FIG. 7. Ultrasound energy scattered back along the plurality of tracked beam will be displayed on oscilloscope screen whereby the tissue layers may be displayed. The tissue region 210 may therefore be viewed and the apparent thicknesses of the various tissue layers may be measured.

The image of the tissue region 210 will show the tissue layer 224 having an undistorted apparent thickness $T_{ud}$ in the absence of any acoustical contrast fluid. The thickness $T_{ud}$ as displayed on the oscilloscope screen may be related to the actual thickness of the tissue layer 224 by knowing the velocity of sound ($C_{tissue}$) within the tissue region 224.

Figure 8:
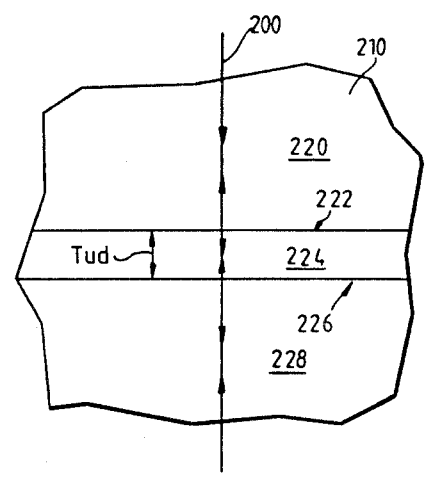
FIG. 8 shows the tissue region of FIG. 7 into which an acoustical contrast fluid has been introduced.

In FIG. 8, an acoustical contrast fluid 230 has been introduced into the tissue region 210. The tissue layer 224 is now seen to have an apparent thickness $T_d$ which is less than the undistorted apparent thickness $T_{ud}$ of the tissue region 224 is FIG. 7. The acoustical contrast fluid 230 is assumed to have a known velocity of sound which is greater than the velocity of sound in the tissue region 210. The distorted thickness $T_d$ is less than the undistorted thickness $T_{ud}$ because ultrasound is now traveling faster through tissue layer 224. The actual thickness of the layer 224 is unchanged while the apparent thickness of the layer 224 is less in the displayed ultrasound image.

Those skilled in the medical ultrasound art will recognize that the velocity of sound within the region 210 in FIG. 8 will principally be determined by three quantities. These quantities are the velocity of sound in region 210 in the absence of any acoustical contrast fluid, the velocity of sound within the acoustical contrast fluid introduced, and the volume concentration of the acoustical contrast fluid within the region 210. Based on principles well known in the ultrasound art, the undistorted thickness $T_{ud}$ will be related to the distorted thickness $T_d$ by the following equation:

$$\frac{T_{ud}}{T_d} = 1 + V_{fluid}\left[\frac{C_{fluid}}{C_{tissue}} - 1\right] \quad (3)$$

where $T_{ud}$ = undistorted thickness $T_d$ = distorted thickness $V_{fluid}$ = volume concentration of acoustical contrast fluid $C_{fluid}$ = sound velocity in the acoustical contrast fluid $C_{tissue}$ = sound velocity of the tissue in the absence of the acoustical contrast fluid.

The volume concentration of the acoustical contrast fluid may be determined from equation (3). The quantity $C_{tissue}$ is first measured. The method and apparatus disclosed in my copending U.S. patent application No. 791,719 may be used. Alternatively, any suitable means and method for sound velocity may be used. The quantity $C_{fluid}$ is known and available for commonly used acoustical contrast fluid, and may also be measured by methods well known in the art. The ratio of the apparent thicknesses $T_{ud}$ and $T_d$ may be determined by means of ultrasound imaging as previously disclosed.

A different measurement technique is used which will improve the measurement accuracy. The ratio $T_{ud}/T_d$ may be shown to be substantially equal to the ratio $$\frac{C_{tissue+fluid}}{C_{tissue}}$$

where $C_{tissue+fluid}$ = Sound velocity in the tissue in the presence of the acoustical contrast fluid. Then, $$\frac{C_{tissue+fluid}}{C_{tissue}} = 1 + V_{fluid}\left[\frac{C_{fluid}}{C_{tissue}} - 1\right] \quad (4)$$

Thus, the volume concentration of the acoustical contrast fluid may be determined from equation (4). This will require that the velocity of sound be measured in the tissue in the region containing the contrast fluid.

Figure 9A:
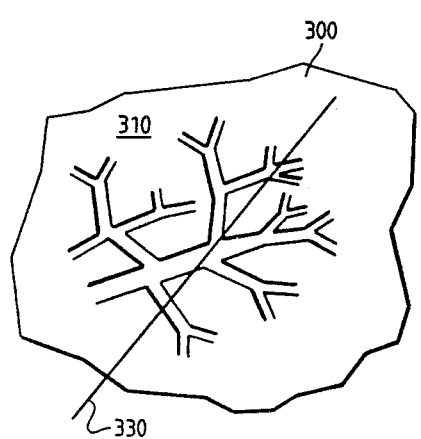
FIG. 9A shows a tissue region and a blood vessel system in a body subjected to an atmospheric pressure of 1 atmosphere.
Figure 9B:
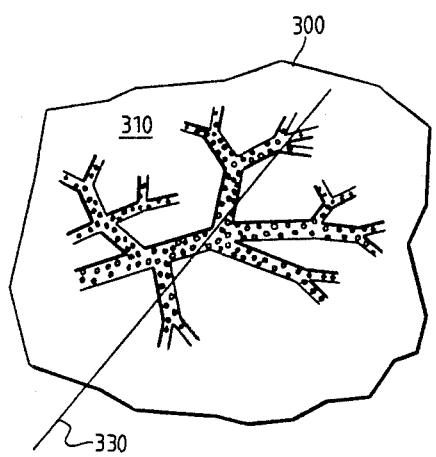
FIG. 9B shows nitrogen bubble formation in the blood vessel system when the body is subjected to decompression.

Refractive effects of a naturally-occurring acoustical contrast fluid are shown in FIGS. 9A and 9B. In FIG. 9A, a tissue region 300 is shown containing a blood vessel system 310. A tracked beam 330 is directed through the region 300. FIG. 9A illustrates the tissue region 300 when the body is subjected to a normal atmospheric pressure of one atmosphere. In FIG. 9B, bubbles of nitrogen 320 (not shown to scale) have formed within the blood vessel system 310 due to the body being subjected to decompression. The velocity of sound within the tissue region 300 will thus be correspondingly reduced because the sound velocity within the nitrogen is less than that within the tissue. As the concentration of nitrogen within the blood vessel system 310 increases, the average sound velocity through region 300 will decrease correspondingly. The increase in concentration of the nitrogen bubbles 320 may be measured by a continuous monitoring of the velocity of sound within the tissue region 300 employing intersecting tracked and tracking beams in a manner disclosed herein and in my copending U.S. patent application No. 791,719.

Equation (3) does not strictly hold when the acoustical contrast fluid is a gas. However, the introduction of very small concentrations of gas into tissue is known in the art to produce relatively large decreases in tissue sound velocity. For example, it has been shown that gas concentrations of from 0.6% to 0.7% can cause the velocity in tissue to reduce from about 1,540 meters per second to about 1,200 meters per second. Thus, small changes in gas concentration may be detected by measuring ultrasound velocity in the tissue.

Although the invention has been described with a certain degree of particularity, it is understood that the description of the preferred embodiment has been only by way of example. Numerous other changes will be apparent to those reading the specification without departing from the spirit and scope of the invention as claimed.

What is claimed is:

1. A method of enhancing the accuracy of in vivo sound velocity estimation in organic tissue along a transducer generated tracked ultrasound beam, characterized by the steps of:
    (a) applying composite tracked ultrasound transducers to the outer skin of a body containing said organic tissue;
    (b) partitioning said tracked beam into a plurality of contiguous segments, each segment having an estimated average velocity substantially different from its adjacent neighbor segments;
    (c) intersecting said tracked beam with a plurality of transducer generated tracking ultrasound beams, said tracking beams being substantially parallel, an angle of incidence defined by the angle between said tracked beam and a line normal to said tracking beams;
    (d) employing a means for measuring the energy and time duration of signal pulses produced by said ultrasound transducers;
    (e) determining the location of the centroids of the pulses produced by said ultrasound transducers;
    (f) measuring a first travel time for a pulse of ultrasound energy to travel between the ultrasound transducer producing the first tracking beam and the ultrasound transducer producing the tracked beam, based upon the baseline-to-centroid distance, on a time scale, of the pulses produced by said transducers;
    (g) measuring a second travel time for a pulse of ultrasound energy to travel between the ultrasound transducer producing the second tracking beam and the ultrasound transducer producing the tracked beam, based upon the baseline-to-centroid distance, on a time scale, of the pulses produced by said transducers;
    (h) computing the difference between said first and second travel times;
    (i) repeating steps (a) through (h) for each of a plurality of preselected values for the angle of incidence; and
    (j) fitting the plurality of data pairs so derived to the equation:

$$t = \frac{\Delta X}{\hat{c}} \cdot \frac{1 + \sin(K_0 + K_1\theta')}{\cos(K_0 + K_1\theta')}$$

to numerically determine the values of $K_0$, $K_1$ and c and thereby yield a value for t wherein t is the travel time, $\Delta X$ is the distance separating tracking beams, $\hat{c}$ is the average speed of sound along a tracked beam between two points, $K_0$ is the equal to one minus one divided by the index of refraction, $K_1$ is equal to one divided by the index of refraction and $\theta'$ is the angle of incidence.

2. A method of enhancing the accuracy of in vivo sound velocity estimation in organic tissue along a transducer generated tracked ultrasound beam, characterized by the steps of:

(a) applying ultrasound transducers to the outer skin of a body containing said organic tissue;

(b) partitioning said tracked beam into a plurality of contiguous segments, each segment having an estimated average velocity substantially different from its adjacent neighbors segments;

(c) intersecting said tracked beam with a plurality of transducer generated tracking ultrasound beams, said tracking beam being substantially parallel, an angle of incidence between said tracked beam and a line normal to said tracking beams being varied through a plurality of values;

(d) employing a means for measuring the energy and time duration of pulses produced by said ultrasound transducers;

(e) determining the location of the centroids of the pulses produced by said ultrasound transducers;

(f) measuring a first travel time for a pulse of ultrasound energy to travel between the ultrasound transducer producing the first tracking beam and the ultrasound transducer producing the tracked beam, based upon he baseline-to-centroid distance, on a time scale, of the pulses produced by said transducers;

(g) measuring a second travel time for a pulse of ultrasound energy to travel between the ultrasound transducer producing the second tracking beam and the ultrasound transducer producing the tracked beam, based upon the baseline-to-centroid distance, on a time scale, of the pulses produced by said transducers;

(h) computing the difference between said first and second travel times;

(i) repeating steps (a) through (h) for each of a plurality of preselected values for the angle of incidence;

(j) computing the average of said travel time differences;

(k) recording the average of said travel time differences together with the value of said angle of incidents to form a data pair;

(l) repeating steps (a) through (k) for a plurality of values of said angle of incidence; and (m) fitting the plurality of data pairs to the equation:

$$t = \frac{\Delta X}{\hat{c}} \frac{1 + \sin(K_0 + K_1 \theta')}{\cos(K_0 + K_1 \theta')}$$

to numerically determine the values of $K_0$, $K_1$ and $\hat{c}$ and thereby yield a value for t wherein t is the travel time, $\Delta X$ is the distance separating tracking beams, $\hat{c}$ is the average speed of sound along a tracked beam between two points, $K_0$ is the equal to one minus one divided by the index of refraction, $K_1$ is equal to one divided by the index of refraction and $\theta'$ is the angle of incidence.

3. The method of claim 1 or claim 2, further characterized by improving the degree of intersection of said tracking beam with said tracked beams by adjusting the position of said tracking beam transducers or maximum integrated amplitude of said ultrasound pulses.

4. The method of claim 1 or claim 2, further characterized by improving the degree of intersection of said tracking beam and said tracked beams by adjusting the position of said tracked beam transducer for maximum integrated amplitude of said ultrasound pulses.

5. The method of claim 1 or claim 2 wherein the direction of travel of said tracked beam and said tracking beam are reversed.

6. A method of enhancing the accuracy of in vivo sound velocity measurements in organic tissue along a transducer generated tracked ultrasound beam, characterized by the steps of:

(a) measuring a time required for an ultrasound pulse to travel a distance along said tracked beam, based upon the baseline-to-centroid distance, on a time scale, of pulses produced by a plurality of tracking beam transducers and said tracked beam transducer;

(b) recording said time together with said distance travelled to form a data pair;

(c) repeating steps (a) and (b) whereby a plurality of data pairs are recorded;

(d) plotting said data pairs;

(e) determining the number of stair steps present in said plot; and (f) estimating the number of scatterers in the tissue from the number of stair steps in order to diagnose the presence of disease in the tissue.

7. The method of claim 6, further comprising repeating steps (a) through (f) for a plurality of training sets, each training set comprising a plurality of examples of tissue, the examples of tissue within each training set being characterized for the presence of disease, whereby an average number of scatterers is computed for each of said plurality of training sets.

8. The method of claim 7, further comprising characterizing an example of tissue under diagnosis for disease by comparing the number of scatterers in said tissue example with the average number of scatterers computed for each of the plurality of training sets.

9. The method of claim 6, further comprising repeating steps (a) through (e) for a plurality of training sets, each training set comprising a plurality of examples of tissue, the examples of tissue within each training set being characterized for the presence of disease, whereby an average number of stair steps is computed for each of said plurality of training sets.

10. The method of claim 9, further comprising characterizing an example of tissue under diagnosis for disease by comparing the number of stair steps in a distance vs. time plot for said tissue with the average number of stair steps computed for each of the plurality of training sets.

11. A method of enhancing the accuracy of in vivo sound velocity estimation in organic tissue along a transducer generated tracked ultrasound beam, characterized by the steps of:

(a) applying composite tracked ultrasound transducers to the outer skin of a body containing said organic tissue;

(b) partitioning said tracked beam into a plurality of contiguous segments, each segment having an estimated average velocity substantially different from its adjacent neighbor segments;

(c) intersecting said tracked beam with a plurality of transducer generated tracking ultrasound beams, said tracking beams being substantially parallel, an angle of incidence defined by the angle between said tracked beam and a line normal to said tracking beams;

(d) employing a means for measuring the energy and time duration of signal pulses produced by said ultrasound transducers;

(e) determining the location of the centroids of the pulses produced by said ultrasound transducers;

(f) measuring a first travel time for a pulse of ultrasound energy to travel between the ultrasound transducer producing the first tracking beam and the ultrasound transducer producing the tracked beam, based upon the baseline-to-centroid distance, on a time scale, of the pulses produced by said transducers;

(g) measuring the undistorted apparent thickness of tissue layers in the region of tissue where said beams intersect;

(h) injecting a preselected volume of acoustical contrast fluid into said region;

(i) imaging said region with ultrasound in the presence of said acoustical contrast fluid whereby a distorted apparent thickness of tissue layers in the region is measured; and (j) deriving the speed of sound in said region in the absence of said acoustical contrast fluid using the equation:

$$\frac{T_{ud}}{T_d} = 1 + V_{fluid}\left[\frac{C_{fluid}}{C_{tissue}} - 1\right]$$

12. A method of enhancing the accuracy of in vivo sound velocity estimation in organic tissue along a transducer generated tracked ultrasound beam, characterized by the steps of:

(a) applying composite tracked ultrasound transducer to the outer skin of a body containing said organic tissue;

(b) partitioning said tracked beam into a plurality of contiguous segments, each segment having an estimated average velocity substantially different from its adjacent neighbor segments;

(c) intersecting said tracked beam with a plurality of transducer generated tracking ultrasound beams, said tracking beams being substantially parallel, an angle of incidence defined by the angle between said tracked beam and a line normal to said tracking beams;

(d) employing a means for measuring the energy and time duration of signal pulses produced by said ultrasound transducers;

(e) determining the location of the centroids of the pulses produced by said ultrasound transducers;

(f) measuring a first travel time for a pulse of ultrasound energy to travel between the ultrasound transducer producing the first tracking beam and the ultrasound transducer producing the tracked beam, based upon the baseline-to-centroid distance, on a time scale, of the pulses produced by said transducers;

(g) measuring an undistorted apparent thickness of a tissue layer in a region of said tissue from an ultrasound image of said region;

(h) injecting an acoustical contrast fluid into said region;

(i) measuring a distorted apparent thickness of said tissue layer from the ultrasound image of said region; and (j) deriving the volumetric concentration of said acoustical contrast fluid using the equation:

$$\frac{T_{ud}}{T_d} = 1 + V_{fluid}\left[\frac{C_{fluid}}{C_{tissue}} - 1\right]$$

13. The method of claim 11 or claim 12, wherein said acoustical contrast fluid is a gas.

14. The method of claim 11 or claim 12, wherein said acoustical contrast fluid is a liquid, the speed of sound in the liquid being substantially known, the liquid selected to be nontoxic to said tissue.

15. A method of enhancing the accuracy of in vivo sound velocity estimation in organic tissue along a transducer generated tracked ultrasound beam, characterized by the steps of:

(a) measuring the velocity of sound within a tissue region in the absence of acoustical contrast fluid, based upon the baseline-to-centroid distance, on a time scale, of pulses produced by beam generating transducers;

(b) injecting said region with an acoustical contrast liquid that is nontoxic to said tissue and in which the speed of sound is substantially known;

(c) measuring the velocity of sound in said region based upon the baseline-to-centroid distance, on a time scale, of the pulses produced by said transducers; and (d) deriving the volumetric concentration of said acoustical contrast fluid using the equation:

$$\frac{C_{tissue+fluid}}{C_{tissue}} = 1 + V_{fluid}\left[\frac{C_{fluid}}{C_{tissue}} - 1\right]$$

* * * * *